United States Patent [19]
Bhatta

[11] Patent Number: 5,375,589
[45] Date of Patent: Dec. 27, 1994

[54] UNIQUE CLEANING CATHETER

[76] Inventor: Krishna M. Bhatta, 60 High St., Skowhegan, Me. 04976

[21] Appl. No.: 138,916

[22] Filed: Oct. 18, 1993

[51] Int. Cl.5 .................... A61B 1/00; A61M 25/00
[52] U.S. Cl. ......................................... 128/4; 604/267
[58] Field of Search ............... 604/266, 267, 49, 50, 604/51, 264, 280; 128/4, 6, 756; 15/104, 4, 106

[56] References Cited

U.S. PATENT DOCUMENTS

| | | | |
|---|---|---|---|
| 4,517,702 | 5/1985 | Jackson | 15/114 |
| 5,090,433 | 2/1992 | Kamaga | 134/169 C |
| 5,140,983 | 8/1992 | Jinotti | 128/207.14 |
| 5,207,213 | 5/1993 | Auhll et al. | 128/6 |
| 5,274,874 | 1/1994 | Cercone et al. | 15/244.1 |
| 5,313,934 | 5/1994 | Wiita et al. | 128/4 |

*Primary Examiner*—J. Yasko
*Assistant Examiner*—Adam J. Cermak
*Attorney, Agent, or Firm*—Hayes, Soloway, Hennessey, Grossman & Hage

[57] ABSTRACT

A unique cleaning catheter adapted for use in conjunction with a fiber optic surgical device comprising an elongate flexible casing having a cleaning brush or the like affixed adjacent its distal end. The cleaning brush or the like is adapted to remove bodily tissue which may accumulate on the distal end of the fiber optic surgical device, without having to completely remove the device from the patient.

10 Claims, 1 Drawing Sheet

UNIQUE CLEANING CATHETER

FIELD OF THE INVENTION

Generally, the present invention relates a unique cleaning catheter. The invention has particular utility in conjunction with a laser probe or other optical fiber, and will be described in connection with such utility, although other utilities are contemplated by the instant invention.

BACKGROUND OF THE INVENTION

In recent years, fiber optic technology has revolutionized medical procedures. Nowhere have the advantages engendered by these advances been greater than in the area of surgical techniques. Due to their flexibility and relatively small size, surgical devices incorporating flexible light pipes (such as fiber optics) may be inserted into bodily cavities through relatively small incisions, whereas prior to the advent of this technology, large incisions, and therefore major surgery was required for such access.

Fiber optic surgical devices, once positioned within the bodily cavity, may be used to view body tissues contained within the cavity, and if properly adapted, to cut and remove undesired bodily tissue from the body cavity. It is often particularly useful for such fiber optic cutting devices to use a coherent beam of electromagnetic radiation (e.g. a laser beam) to thermally damage undesired tissues. When struck by a low-power coherent beam, the undesired tissue may be cauterized and the tissue killed.

It is necessary in such procedures that the coherent beam be directed in a precise manner upon undesired tissue to avoid destruction or removal of healthy, desired tissue. Positioning of the beam is generally achieved by inserting a relatively stiff catheter to serve as mechanical support and guide to the flexible optical fiber. Fiber optic viewing devices are typically carried within the catheter to allow a surgeon to view the target area for initial positioning and for subsequent viewing of the target area during operation. Once the catheter is positioned adjacent the target tissue, the fiber optic cutting device is inserted through the catheter and extended slightly past its distal end in close proximity to the target tissue. The coherent beam of electromagnetic radiation may then be supplied through the cutting device to illuminate and destroy undesired tissue.

When this occurs, the efficiency of the procedure is significantly reduced. One consequence of tissue accumulation on the fiber is increased difficulty in positioning the fiber adjacent the target tissue. The fiber optic viewing device can become blocked by the tissue, thereby impairing the surgeon's view of the probe to the point where continued operation may become impossible.

Tissue which accumulates on the distal end of the optical fiber may act as an insulator between the fiber optic device and the undesired tissue and absorb some of the beam energy directed upon the target tissue. In order to maintain sufficient beam strength to cauterize the undesired tissue as bodily tissue accumulates on the fiber, it is necessary either to increase the intensity of the beam, or to clean the tissue from the fiber. Beam intensity, however, is a critical factor in fiber optic procedures.

To overcome these problems, therefore, it currently is necessary periodically to remove the fiber from the patient, for cleaning. This cumbersome procedure not only adds a significant amount of time to fiber optic surgery, but also prolongs patient discomfort. Accordingly, there is a need in the art for a more efficient means of cleaning the distal end of a fiber optic probe during surgery.

There have been attempts at providing a catheter system having a means for cleaning the distal end of a catheter as it is withdrawn from a patient. For example, Jinotti, U.S. Pat. No. 5,140,983, discloses a Multipurpose Catheter Assembly with a sponge attached to the assembly for cleaning the catheter as it is withdrawn from a patient. The sponge is affixed to the inner wall of the assembly which is located outside of a patient. The catheter slides through an opening in the sponge and into the patient. When the catheter is withdrawn, the sponge cleans its distal end of mucus and other bodily fluids.

Although providing somewhat effective means for removing undesired tissues after a catheter is withdrawn from a patient, Jinotti's sponge is located outside of the body in a separate assembly. Accordingly, Jinotti fails to address the cleaning of a fiber optic device inside the body using a cleaning means affixed to the interior wall of a catheter. In fact, Jinotti fails to recognize the unique problems associated with the build up of bodily tissue on fiber optic devices during medical procedures.

SUMMARY OF THE INVENTION

Accordingly, there is provided, in accordance with one aspect of the present invention, a cleaning catheter adapted for insertion into a narrow or confined body cavity. The catheter contemplated by the present invention comprises an elongate casing that has proximal and distal ends, and including an optical fiber means for delivering a coherent beam of electromagnetic radiation (i.e. laser energy) to a target tissue when the instrument is inserted into the bodily cavity. The optical fiber means is movable within the casing for positioning nearby the target tissue. Means for cleaning the optical fiber are affixed to the casing proximal to the distal end. During operation, the fiber is extended past the distal end of the catheter to illuminate the target tissue. Should tissue begin to build up on the fiber, the device may be withdrawn into the catheter and moved in and out in contact with the cleaning means which removes the tissue. Thus, the fiber optic device may be cleaned of body tissue during a surgical procedure without completely removing the device from the patient.

BRIEF DESCRIPTION OF THE DRAWINGS

Other aspects, features, advantages, and utilities of the present invention will become apparent, as the following description proceeds, and upon reference to the hereinafter appended drawings wherein like numerals represent like parts, and wherein.

While the present invention will hereinafter be described in connection with a preferred embodiment and method of use, it will be understood that it is not intended to limit the invention to this embodiment or method of use. On the contrary, it is intended to cover all alternatives, modifications, and equivalents as may be included within the spirit and broad scope of the invention as defined by the hereinafter appended claims .

DESCRIPTION OF THE PREFERRED EMBODIMENT

Figure 1:
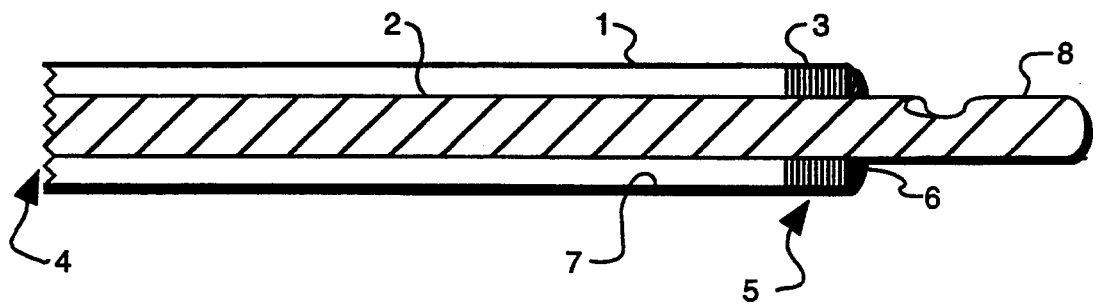
FIG. 1 is a side view of the preferred embodiment of the cleansing catheter made in accordance with the present invention; depicted in FIG. 1.

Turning to FIG. 1, a side view of a preferred form of cleaning catheter device made in accordance with and useful in accordance with the instant invention is depicted. The device comprises an elongate casing 1 having a proximal 4 and distal end 5. An optical fiber 2 (i.e. a laser probe)is included within the casing 1. The fiber 2 is movable within the casing 1 and may be extended through the opening 6 at the distal end 5 of the casing for positioning nearby the target tissue (not shown). The fiber 2 terminates at or adjacent the proximal end 4 of the casing 1. A cleaning means 3 is affixed to the interior surface 7 of the casing adjacent its distal end 5, and extends radially inwardly from the interior surface. The cleaning means 3 is adapted for removing bodily tissue accumulated at the distal end 8 of the fiber 2 when the fiber is placed into frictional contact with the cleaning means.

Figure 2:
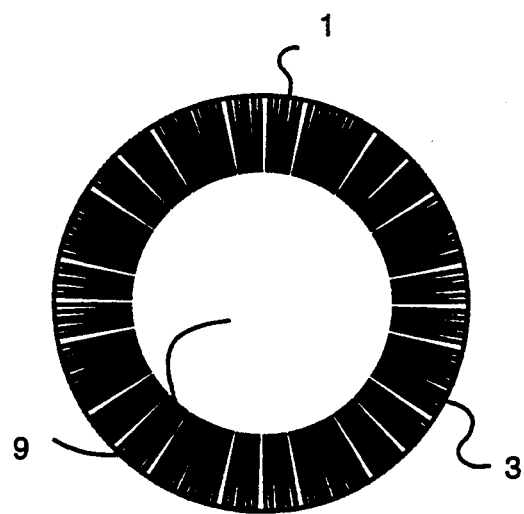
FIG. 2 is an end view of the device made in accordance with the present invention without the fiber optic device installed.

Referring also to FIG. 2, the cleaning means 3 extends radially inward from the interior wall of the casing 1 leaving an opening 9 for the fiber 2 (FIG. 1) to pass through while coming into frictional contact with the cleaning means 3. Depending on the shape of the optical fiber 2 to be cleaned, the cleaning means 3 define a variety of shapes for the opening 9 such as cylindrical, conical, semi-cylindrical etc. Although, the preferred embodiment employs a brush, the cleaning means 3 may comprise any flexible surface capable of removing tissue when in frictional contact with the distal end 8 of the fiber 2.

A preferred method of using the cleaning catheter made according to the instant invention will now be described. First, the casing 1 of the catheter device is inserted into a body cavity. The casing 1 is then advanced through the cavity until its distal end 5 is positioned adjacent the target tissue. The distal end 8 of the optical fiber 2 carried within the casing 1 is then extended forward of the distal end 5 of the casing in close proximity or in contact with the target tissue. Then radiation is delivered continuously or sporadically, as needed, by optical fiber 2 to "cook" the target tissue, thermally destroying the tissue and cauterizing any blood therein. Should bodily tissue accumulate on the optical fiber 2 the fiber may be withdrawn into the casing 1 and moved in and out thereby causing the distal end 8 of the fiber to come into frictional contact with the cleaning means 3 affixed to the interior wall 7 of the casing. Frictional contact between the fiber 2 and the cleaning means 3 removes the tissue attached to the distal end 8 of fiber. The fiber 2 may then be extended forward of the distal end 5 of the casing 1 for continued removal of target tissue.

It is evident there has been provided, in accordance with the present invention, a unique cleaning catheter and an improved procedure for optical treatment and removal of selected tissues. While this invention has been described in conjunction with a specific embodiment thereof, various alternatives and modifications may be made without departing from the spirit and scope of the invention. The invention advantageously may be used with a variety of fiber optic devices, e.g. ADD—laserscope, and using video technology. Additionally, the device of the present invention may comprise a two-way proximal converter, one for the optical fiber and the other for supplying an irrigating fluid during surgery. Also, the catheter may be made of a material that does not absorb the electromagnetic radiation (i.e., laser energy) supplied to the tissue sight by the optical fiber. Moreover, the catheter device of the present invention may be adapted to permit the distal end of the optical fiber to be placed inside the distal end of the catheter but proximal to the cleaning means.

These modifications may be combined in a single embodiment so that when electromagnetic radiation is discharged through the optical fiber, it is transmitted through the catheter and is discharged into the target tissue on a desired time area basis. Simultaneous with discharge of the electromagnetic radiation through the catheter wall, an irrigating fluid may be supplied through the instrument by way of the two-way proximal converter. Advantageously, this arrangement permits the instrument to avoid contact of the delivery fiber with the target tissue. Accordingly, it is intended to embrace all such alternatives, modifications, and variations that fall within the spirit and broad scope of the hereinafter appended claims.

What is claimed is:

1. A self-cleaning surgical instrument insertable into a patient and comprising a catheter including:
   a. an elongate casing having a proximal and a distal end;
   b. optical fiber means having a proximal and a distal end for delivering a coherent beam of electromagnetic radiation to a target tissue adjacent the distal end of said casing, said optical fiber means carried within said casing and movable within said casing for positioning its distal end proximal to said target tissue; and
   c. mechanical cleaning means carried on the inside of the distal end of said casing, said cleaning means being adapted to remove bodily tissue from the distal end of said optical fiber means through wiping contact of said fiber means with said cleaning means by movement of said fiber means relative to said cleaning means in said catheter, without necessitating removal of said instrument from said patient.

2. An instrument according to claim 1, wherein said cleaning means comprises a brush.

3. An instrument according to claim 1, wherein said cleaning means is affixed to an interior surface of said casing and substantially fills said distal end of said casing.

4. An instrument according to claim 1 having a two way proximal converter, one for said optical fiber means and the other for irrigation.

5. An instrument according to claim 4, wherein the catheter is made of material that does not absorb the radiation being delivered by said fiber means.

6. An instrument according to claim 5, and further comprising means for delivering an irrigating fluid through said instrument to contact said target tissue.

7. An instrument according to claim 6, wherein said cleaning means comprises a brush affixed to an interior surface of said casing and substantially filling said distal end of said casing.

8. An instrument according to claim 1, wherein said cleaning means comprises a flexible member extending circumferentially from the interior of said casing.

9. An instrument according to claim 8, wherein said flexible member substantially fills the distal end of said casing.

10. In a method of thermally treating a target tissue within a body by means of electromagnetic radiation delivered from an optical delivery fiber having a proximal and a distal end carried within a catheter having an elongate casing having a proximal and distal end, wherein tissue may accumulate on the distal end of the fiber, the improvement which comprises removing tissue from the distal end of said optical delivery fiber by frictionally engaging the optical delivery fiber with a cleaning means carried on an interior surface of the distal end of said casing of said catheter.

* * * * *